(12) United States Patent
Netravali et al.

(10) Patent No.: US 11,185,373 B2
(45) Date of Patent: Nov. 30, 2021

(54) METHOD FOR RECOVERING A REGISTRATION OF A BONE

(71) Applicant: THINK SURGICAL, INC., Fremont, CA (US)

(72) Inventors: Nathan A. Netravali, Fremont, CA (US); Feimo Shen, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 42 days.

(21) Appl. No.: 16/080,766

(22) PCT Filed: Mar. 1, 2017

(86) PCT No.: PCT/US2017/020175
§ 371 (c)(1),
(2) Date: Aug. 29, 2018

(87) PCT Pub. No.: WO2017/151751
PCT Pub. Date: Sep. 8, 2017

(65) Prior Publication Data
US 2019/0021798 A1 Jan. 24, 2019

Related U.S. Application Data

(60) Provisional application No. 62/302,773, filed on Mar. 2, 2016.

(51) Int. Cl.
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 90/361* (2016.02); *A61B 90/39* (2016.02);
(Continued)

(58) Field of Classification Search
None
See application file for complete search history.

(56) References Cited

U.S. PATENT DOCUMENTS 5,086,401 A 2/1992 Glassman et al.
6,033,415 A 3/2000 Mittelstadt et al.
(Continued)

FOREIGN PATENT DOCUMENTS

WO 2004069073 A2 8/2004
WO 2006091494 A1 8/2006

*Primary Examiner* — Nancy Bitar
(74) *Attorney, Agent, or Firm* — Blue Filament Law PLLC

(57) ABSTRACT

A method for re-registration between a robotic coordinate system and an image data set is provided. The inventive re-registration method includes the steps of providing an image data set that has been registered within a robotic coordinate system based on an initial bone position; locating a first conserved point and a line segment that is fixed relative to the initial bone position prior to any detectable change in bone position from the initial bone position; relocating the first conserved point and at least a portion of the line segment after bone motion may have occurred to determine the locational change in the first conserved point and the line segment; and re-registering the image data set within the robotic coordinate system based on the determined locational changes. A system for performing this method is also provided.

13 Claims, 5 Drawing Sheets

(52) U.S. Cl.
CPC . *A61B 2034/2055* (2016.02); *A61B 2090/364* (2016.02); *A61B 2090/3916* (2016.02)

(56) References Cited

U.S. PATENT DOCUMENTS

| | | | |
|---|---|---|---|
| 6,061,644 A | 5/2000 | Leis | |
| 6,322,567 B1 | 11/2001 | Mittelstadt et al. | |
| 6,430,434 B1 * | 8/2002 | Mittelstadt | A61B 17/175 600/426 |
| 7,043,961 B2 | 5/2006 | Pandey et al. | |
| 7,206,626 B2 | 4/2007 | Quaid, III | |
| 8,224,024 B2 | 7/2012 | Foxlin et al. | |
| 8,287,522 B2 | 10/2012 | Moses et al. | |
| 8,876,830 B2 | 11/2014 | Hodorek et al. | |
| 8,945,137 B1 * | 2/2015 | Greenhalgh | A61B 17/8802 606/99 |
| 8,961,536 B2 | 2/2015 | Nikou et al. | |
| 10,136,948 B2 * | 11/2018 | Jensen | A61B 6/487 |
| 10,531,927 B2 * | 1/2020 | Crawford | A61B 34/74 |
| 2002/0138078 A1 * | 9/2002 | Chappuis | A61B 17/1671 606/85 |
| 2005/0216032 A1 | 9/2005 | Hayden | |
| 2006/0116679 A1 * | 6/2006 | Lutz | A61B 17/80 606/86 B |
| 2007/0289998 A1 * | 12/2007 | Keller | B05C 17/00553 222/137 |
| 2008/0269596 A1 * | 10/2008 | Revie | A61F 2/4603 600/424 |
| 2008/0287781 A1 * | 11/2008 | Revie | A61B 90/36 600/426 |
| 2009/0192519 A1 * | 7/2009 | Omori | A61B 34/30 606/130 |
| 2010/0198218 A1 * | 8/2010 | Manzo | A61B 18/1445 606/45 |
| 2011/0130761 A1 * | 6/2011 | Plaskos | A61B 34/30 606/87 |
| 2013/0060278 A1 | 3/2013 | Bozung et al. | |
| 2014/0039517 A1 | 2/2014 | Bowling et al. | |
| 2014/0378999 A1 * | 12/2014 | Crawford | A61B 17/8866 606/130 |
| 2015/0100066 A1 * | 4/2015 | Kostrzewski | A61B 90/11 606/130 |
| 2015/0366624 A1 * | 12/2015 | Kostrzewski | A61B 34/76 606/130 |
| 2016/0225192 A1 * | 8/2016 | Jones | G06F 3/012 |
| 2016/0331467 A1 * | 11/2016 | Slamin | A61F 2/30756 |
| 2017/0042557 A1 * | 2/2017 | Plaskos | A61B 34/30 |
| 2017/0258532 A1 | 9/2017 | Shalayev et al. | |
| 2018/0014888 A1 | 1/2018 | Bonny et al. | |
| 2018/0325608 A1 * | 11/2018 | Kang | A61B 34/30 |
| 2019/0090966 A1 * | 3/2019 | Kang | A61B 34/10 |
| 2019/0223962 A1 * | 7/2019 | Roldan | A61B 34/10 |
| 2019/0314040 A1 * | 10/2019 | Greenhalgh | A61B 17/00234 |

* cited by examiner

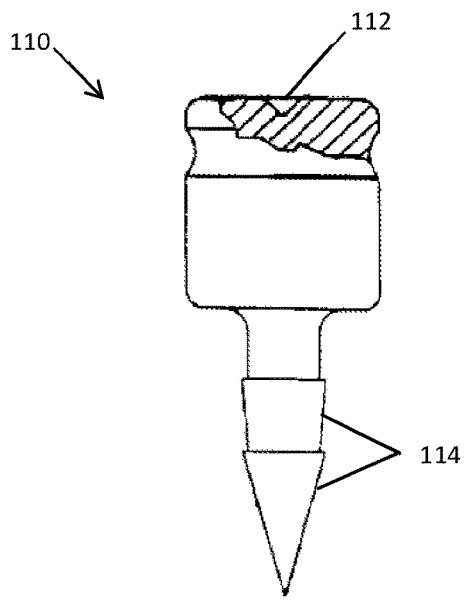
FIG. 1A
(Prior Art)
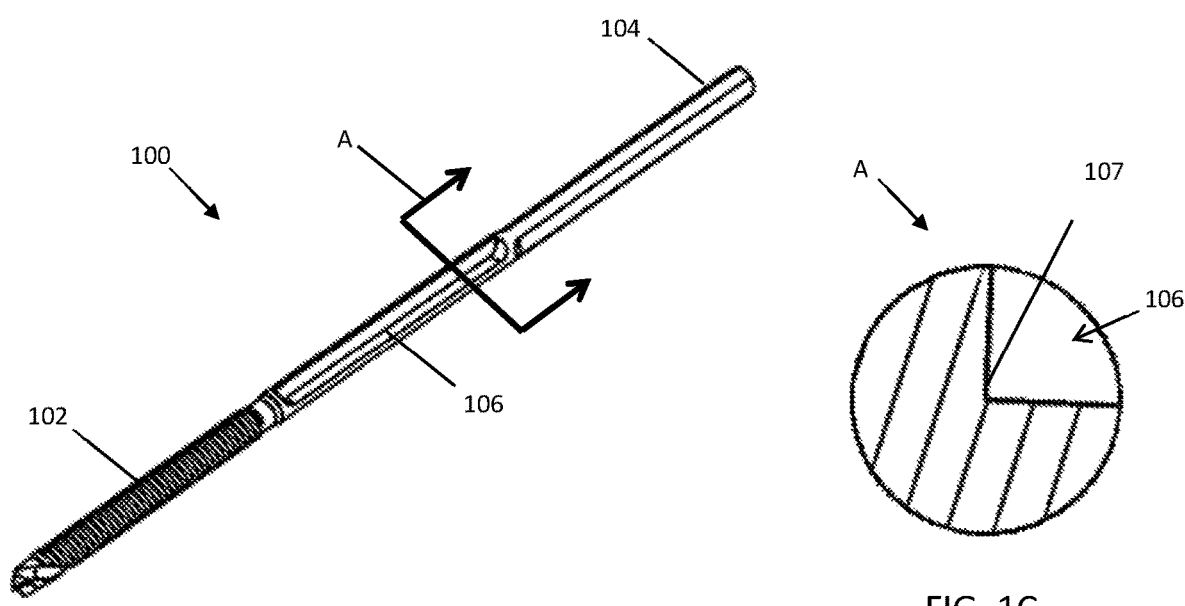
FIG. 1B
FIG. 1C

METHOD FOR RECOVERING A REGISTRATION OF A BONE

RELATED APPLICATIONS

This application claims priority benefit of U.S. Provisional Application Ser. No. 62/302,773 filed Mar. 2, 2016; the contents of which are hereby incorporated by reference.

TECHNICAL FIELD

The present invention generally relates to computer-assisted surgery, and more particularly to a method for recovering a registration during a computer-assisted surgical procedure.

BACKGROUND

Registration of an object (e.g., a rigid bone during a total joint replacement procedure) requires matching the surface of the bone to a pre-existing virtual model of the bone. Once the object moves, a recovery of that registration can be rapidly achieved by locating points on recovery markers that have been placed in known locations on the object prior to the registration. Recovery of all six degrees of freedom (6-DOF) can be accomplished by locating three known points on two recovery markers as described in U.S. Pat. No. 6,430,434. However, this method requires the removal of a portion of one of the recovery markers to collect a point, which may inadvertently introduce error in the registration recovery process.

Another method is to use three individual recovery markers placed on the bone to define the three points. This adds an additional marker to be placed on the bone. Depending on the surgical access to the operating site, this may be difficult, and may also increase the overall operating time.

A third method may use two recovery markers placed on the bone to define the first two recovery points. The third point is collected on the bone in a general area away from the operating site (e.g. the femoral shaft for total hip replacement procedures) using a percutaneous probe. Although this method is accurate, it requires the surgeon to pierce the skin with little knowledge of the underlying anatomy such as critical nerves, arteries and veins.

In certain medical procedures, such as robotic surgery, precision and accuracy are critical. Although robotic surgeries are accurate and repeatable, the surgical times may be increased compared to conventional or manual procedures. Therefore, an efficient registration recovery method is essential in the event the object moves post registration.

Thus, there exists a need for a method to recover a registration of a bone after bone movement during a robotic surgical procedure that requires minimal hardware while maintaining excellent accuracy.

SUMMARY OF THE INVENTION

A method for re-registration between a robotic coordinate system and an image data set is provided. The inventive re-registration method includes the steps of providing an image data set that has been registered within a robotic coordinate system based on an initial bone position; locating a first conserved point and a line segment that is fixed relative to the initial bone position prior to any detectable change in bone position from the initial bone position; relocating the first conserved point and at least a portion of the line segment after bone motion may have occurred to determine the locational change in the first conserved point and the line segment; and re-registering the image data set within the robotic coordinate system based on the determined locational changes. The first conserved point is defined by a first recovery marker and the line segment is defined by a second recovery marker. In certain inventive embodiments, at least one of the first or second recovery markers may be implanted after the image data set has been created and may also be attached intraoperatively to the bone.

A system for registration recovery of a bone includes a point recovery marker attached to the bone at a first position. A groove recovery marker and a bone pin are attached to the bone in fixed relative orientation by a pin clamp. A fiducial marker array extends from the pin clamp and is visible to a camera of an optical tracker.

BRIEF DESCRIPTION OF THE DRAWINGS

The present invention is further detailed with respect to the following drawings that are intended to show certain aspects of the present of invention, but should not be construed as limits on the practice of the invention, wherein:

FIG. 1A depicts a prior art point registration recovery marker;

FIG. 1B depicts a groove registration recovery marker in accordance with embodiments of the invention;

FIG. 1C depicts a cross-section of the groove recovery marker shown in FIG. 1B in accordance with embodiments of the invention.

DETAILED DESCRIPTION

Figure 2:
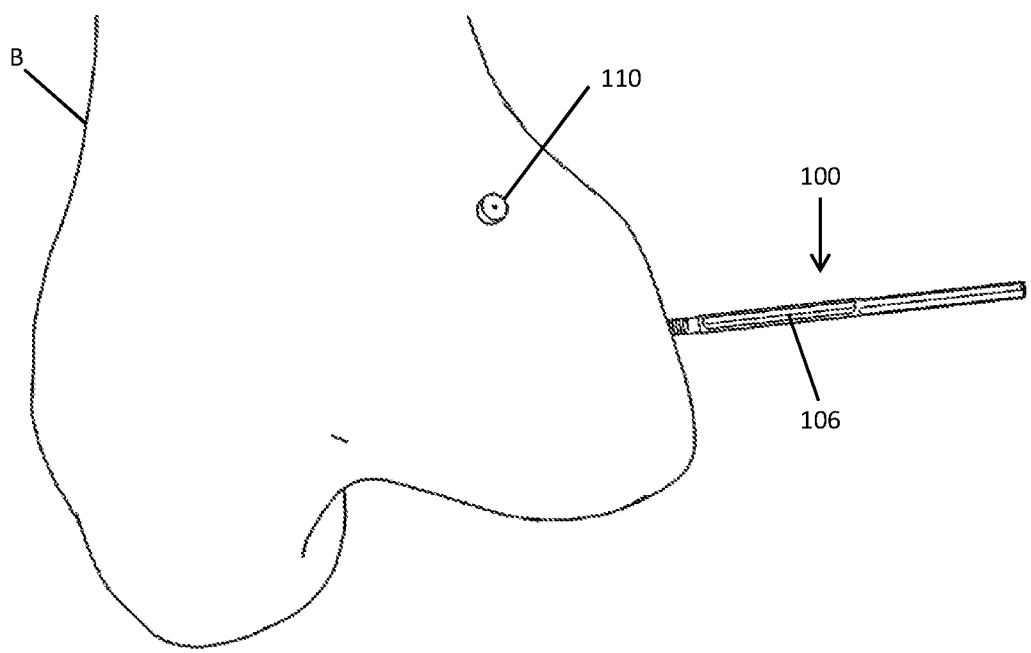
FIG. 2 illustrates the placement of the groove recovery marker and point recovery marker in accordance with embodiments of the invention.

The present invention has utility as a method to recover a bone-to-image, image-to-system, or bone-to-system registration if bone movement occurs during a computer-assisted surgical procedure. The following description of the preferred embodiments of the invention is not intended to limit the invention to these preferred embodiments, but rather to enable any person skilled in the art to make and use this invention.

Embodiments of the present invention may be implemented with a computer-assisted surgical system. Examples of surgical systems that can exploit embodiments of the invention illustratively include a 1-6 degree of freedom hand-held surgical system, a navigated surgical system, a serial-chain manipulator system, a parallel robotic system, or a master-slave robotic system, as described in the following patents and patent applications, all of which are incorporated by reference herein in their entirety: U.S. Pat.

Nos. 5,086,401, 6,033,415, 7,206,626, 8,876,830, and 8,961,536; U.S. Pat. App. Pub. Nos. 2013/0060278 and 2005/0216032; and U.S. Provisional Application No. 62/054,009. The computer-assisted surgical system may provide autonomous, semi-autonomous, haptic, or no control (passive), and any combinations thereof.

Also, referenced herein is the use of a mechanical digitizer arm and an optically tracked probe for collecting various points in the operating room. An example of a mechanical digitizer arm for collecting points is described in U.S. Pat. No. 6,430,434, and an example of an optically tracked probe for collecting points is described in U.S. Pat. No. 7,043,961, both of which are hereby incorporated by reference herein in their entirety. For clarity, the "collection of points" refers to the digitizing, measuring, and/or recording of the location of physical points in space into a reference coordinate frame/system, such as the coordinate frame of a robotic system or a tracking system.

With reference to the figures, FIG. 1A depicts an example of a prior art point recovery marker 110 as described in U.S. Pat. No. 6,430,434. The prior art point recovery marker 110 includes a divot 112 for facilitating the collection of a fixed point, and a bone engaging portion 114 (e.g., a spike, a pin) for engaging a bone. FIG. 1B depicts an example of a groove registration recovery marker 100. The groove recovery marker 100 includes a bone engaging portion 102, a proximal portion 104, and a groove 106 between the bone engaging portion and the proximal portion 104. The bone engaging portion 102 may include threads or flutes to grasp the bone. The proximal portion 104 is configured to assist the user in installing the recovery marker 100 into the bone. In one embodiment, the proximal portion 104 is configured to be received in a driver tool, where the driver tool can drive the groove recovery marker 100 into the bone. The driver tool may be a screwdriver or a drill for example. In other embodiments, the proximal portion 104 has features to allow the user to manually insert the marker 100 into the bone, such as a handle, a butterfly handle, or a grip. The groove 106 facilitates the collection of a series of points along the length of the groove 106. In a particular embodiment, with reference to FIG. 1C, a center axis 107 of the groove 106 is collinear with the longitudinal center axis of the groove recovery marker 100. In a specific embodiment, the groove 106 is an elongated notch having two perpendicular side walls. In a particular embodiment, the groove 106 extends 30%-40% of the overall length of the groove recovery marker 100.

With respect to FIG. 2, a bone B is shown with the point recovery marker 110 installed in the bone B at a first location, and the groove recovery marker 100 installed in the bone B at a second location. Once the two markers are installed, a registration technique known in the art such as point-to-surface as described in U.S. Pat. No. 6,033,415 may be used to register at least one of: (i) the bone B to an image of the bone (bone-to-image); (ii) an image of the bone to the surgical system based on the position of the bone B (image-to-system); and/or (iii) the bone B directly to the system (bone-to-system). The bone may also be registered with respect to the coordinates of a tracking system in communication with a computer-assisted surgical system.

Figure 3A:
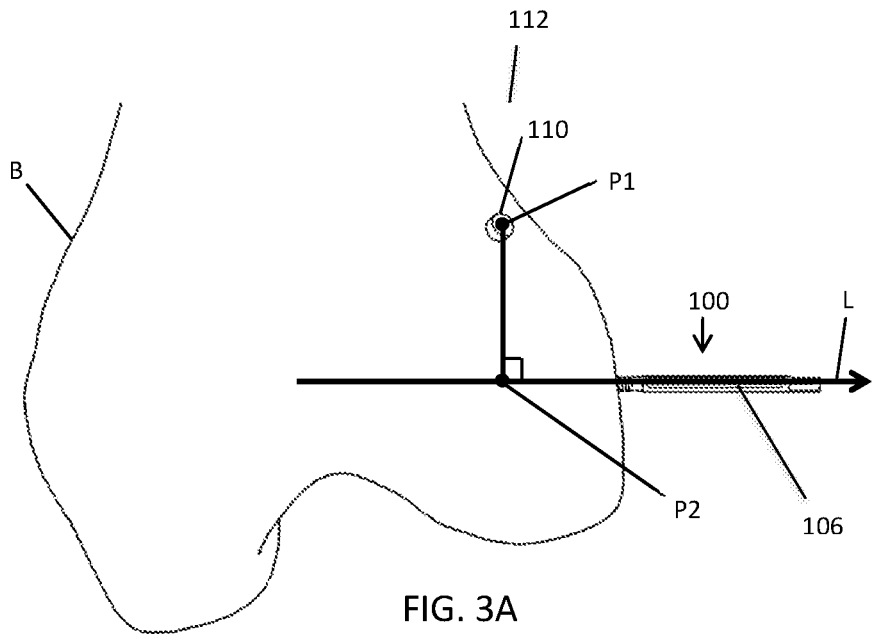
FIG. 3A depicts a process for collecting and calculating a vector and set of points prior to bone movement in accordance with embodiments of the invention.

With respect to FIG. 3A, prior to or after bone registration, but before bone motion the following procedure is executed:
 a. A distal end of a passive digitizer arm, a tracked probe, or a distal end of a robotic surgical system is used to collect fixed point P1 in the divot 112 of the point recovery marker 110.
 b. A distal end of a passive digitizer arm, a tracked probe, or a distal end of a robotic surgical system is used to collet several points (e.g. 10 or more) along the groove 106 of the groove recovery marker 100. The user can simply slide the distal end or probe tip along the groove 106 while the system (e.g. the computer-assisted surgical system, a mechanical digitizer system, or a tracking system) acquires the several points during the sliding action.
 c. The system fits a straight line L to the several acquired points and determines a vector in the direction away from the bone surface (arrow L).
 d. The system calculates the point P2 on the line L that is the closest to P1 (i.e. the perpendicular distance from point P1 to line L. Point P2 is on a line through P1 that is perpendicular to line L.
 e. This defines all 6-DOF.

Figure 3B:
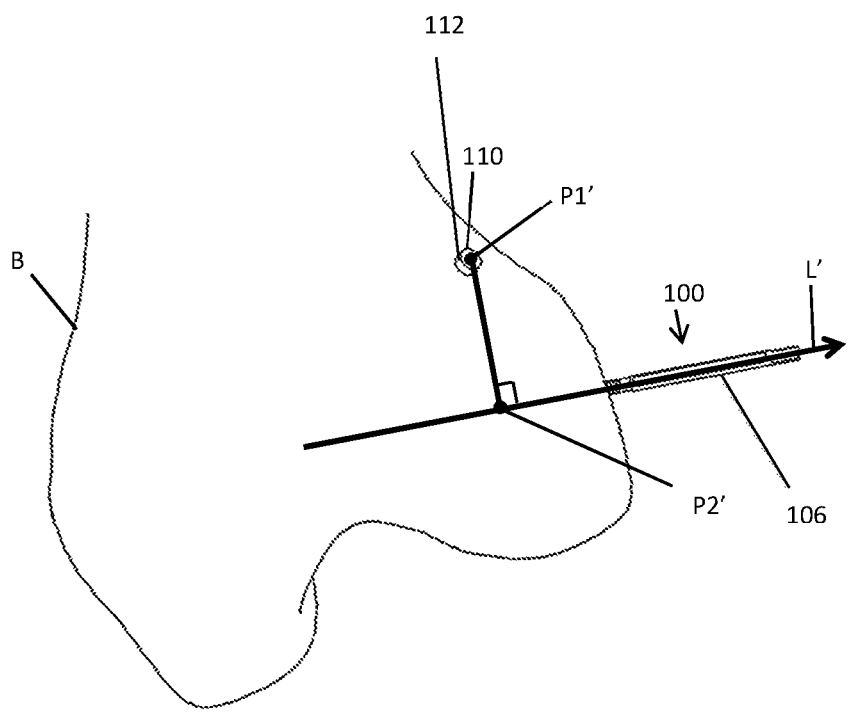
FIG. 3B depicts a process for collecting and calculating a vector and set of points post bone movement in accordance with embodiments of the invention.

With reference to FIG. 3B, after bone motion the following procedure is executed to recover the registration:
 f. Acquire several points on the groove 106 going away from the bone surface as described in step b.
  i. Note, the groove recovery marker 100 can actually move relative to the bone as long as the motion is only a translation in the direction of the groove axis. This is an advantageous feature of the groove recovery marker 100 as further described below. In contrast, for the three-point method as described in U.S. Pat. No. 6,420,434 or using three-point recovery markers, none of the markers can move relative to the bone.
 g. The system fits a straight line L' from the acquired points and determines a vector in the direction away from the bone surface.
 h. Collect fixed point P1' in the divot 112 of the point recovery marker 100.
 i. The system calculates the point P2' on the line L' closest to point P1' using the same method as step d.
 j. The system determines any translational movement, T, of the bone from point P2 to point P2' by subtraction T=P2'-P2.
 k. The system determines any rotational movement, R, of the bone by finding the unit vector about which a single rotation is done, and the scalar amount of rotation angle, theta.
  i. The unit vector about which a single rotation is done can be calculated by taking the cross product between a unit vector along L and a unit vector along L'.
  ii. The scalar amount of rotation angle, theta, can be calculated by taking the dot product between a unit vector along L and a unit vector along L'.
 l. Combine T and R to obtain the transformation matrix M.

The resultant 4×4 matrix M is the matrix for a rigid transformation that completely describes the six degrees of freedom of bone movement. This transformation is used to re-register at least one of the bone-to-image, image-to-system, and/or bone-to-system. In a specific embodiment, the image-data set of the bone is re-registered within a computer-assisted surgical system coordinates or a tracking system coordinates using the transformation matrix M without having to repeat a full registration technique such as point-to-surface registration. Except for theta, all symbols here are math vectors.

Figure 4A:
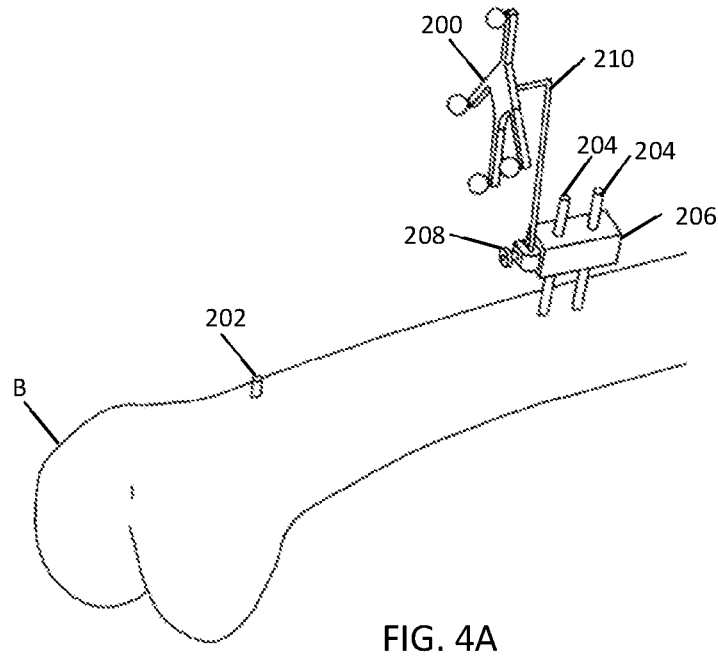
FIG. 4A depicts a prior-art system for tracking a bone with a fiducial marker array.
Figure 4B:
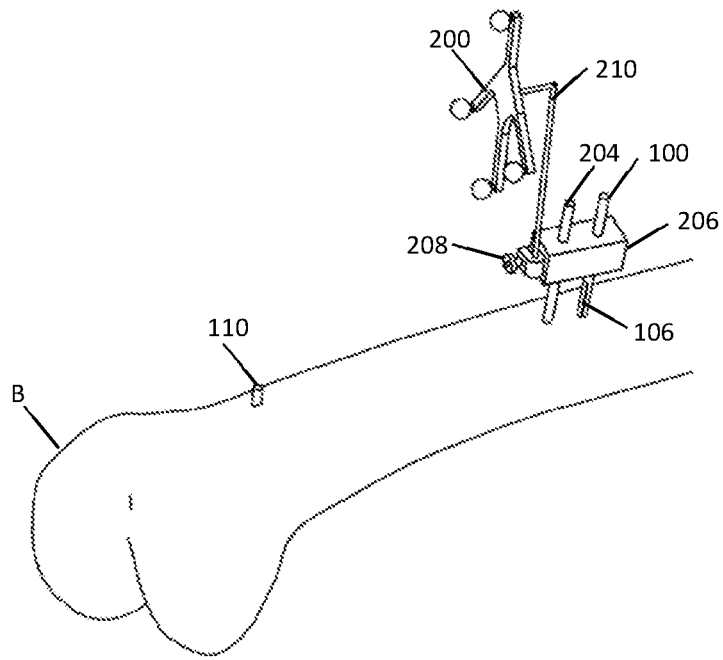
FIG. 4B depicts a system capable of recovering a registration of a tracked bone in accordance with embodiments of the invention.

In a specific inventive embodiment, with reference to FIGS. 4A-4B, a system and method for recovering a registration of a tracked bone is shown. FIG. 4A depicts a prior art system for tracking a bone B with the use of a fiducial marker array 200 fixed to the bone B. The fiducial marker array 200 is fixed to the bone using various components prior to registering the bone B. The components may include two bone pins 204 drilled into the bone, a pin clamp 206 for clamping to the pins 202 in a fixed relative orientation to the bone, and an array clamp 208 for clamping a rod 210 attached to the fiducial marker array 200 to the pin clamp 206. The array clamp 208 is adjustable to allow the user to easily orient the fiducial marker array 200 towards a pair of optical of an optical tracking system prior to clamping and securing the POSE of the array 200 relative to the bone B. A computer is used to calculate bone registration based on camera images. It is imperative that the POSE of the marker array 200 remains rigid with respect to the bone B after the bone B is initially registered; otherwise, the tracking is no longer accurate. Currently, a method to quickly determine whether the marker array 200 has moved relative to the bone B, involves the use of a checkpoint marker 202. The checkpoint marker 202 is inserted directly on the bone B to ensure the checkpoint marker 202 does not move relative to the bone B. Throughout the course of a procedure, the POSE of the marker array 200 relative to the bone B is checked by digitizing the checkpoint marker 202 and determining if the relative POSE of the marker array 200 with respect to the checkpoint marker 202 has changed. If a change is detected at any two-time points during the procedure then the marker array 200 has moved relative to the bone B, and the registration and tracking is no longer accurate. In this case, the surgeon must fully re-register the bone using a time consuming registration technique such as point-to-surface.

Since there is always a chance the marker array 200 may move relative to the bone B, the registration recovery method described herein is well suited for recovering the registration in such a case. With reference to FIG. 4B, the checkpoint marker 202 is replaced with a point recovery marker 110, and one of the bone pins 204 is replaced with the groove recovery marker 100. After the marker array 200 is fixed with respect to the bone B, steps a-k as described above is executed to recover the registration in the event the marker array 200 moves relative to the bone B. It should be appreciated, that although a fiducial marker array 200 is illustratively shown, the same method may be applied to other tracking systems such as a mechanical tracking system having a probe fixed directly to the bone B. Additionally, there is no necessary need to replace the bone pin 204 with the groove recovery marker 100, but rather, a groove recovery marker 100 may be inserted into the bone B in addition to the two bone pins 204 that facilitate the fixation of the marker array 200 to the bone B.

Embodiments of the present invention are advantageous as only two fiducial markers are required to recover the registration, as opposed to three individual markers or two markers and an extender pin. Another advantage is the groove recovery marker 100 can be re-positioned along its axis without affecting the recovery registration process. Occasionally, the recovery markers may be placed in the bone in a position or depth that may impede or come in contact with an end-effector of the computer-assisted surgical system. If the end-effector tool hits the recovery marker, it halts the surgery and may damage the tool. Therefore, the surgeon can unscrew the pin along its longitudinal axis if it appears the end-effector tool may contact the pin.

Robotic System

Figure 5:
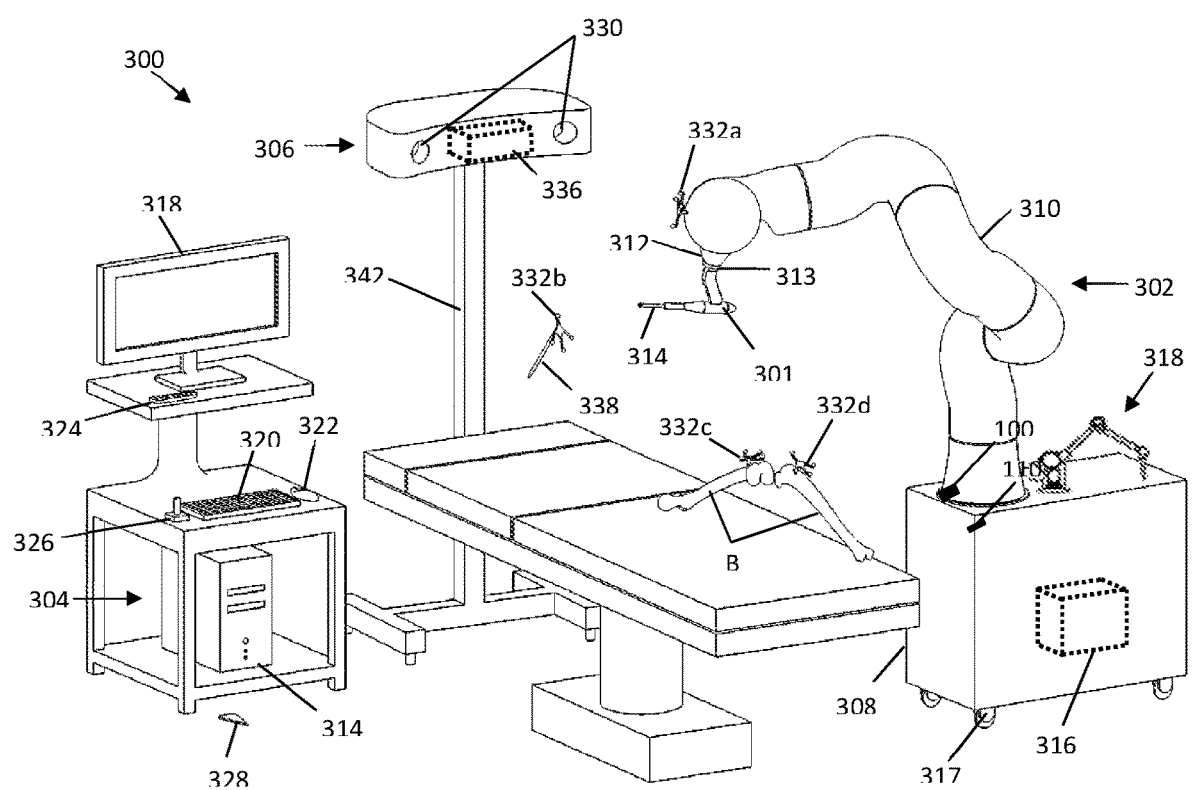
FIG. 5 depicts a robotic system for recovering a registration of a bone in accordance with embodiments of the invention.

With reference to FIG. 5, an embodiment of a robotic surgical system is shown generally at 300 capable of implementing embodiments of the inventive method for registration recovery of a bone. The surgical system 300 generally includes a surgical robot 302, a computing system 304, and may include at least one of a mechanical digitizer arm 318 and/or an optical tracking system 306.

The surgical robot 302 may include a movable base 308, a manipulator arm 310 connected to the base 308, an end-effector flange 312 located at a distal end of the manipulator arm 310, and an end-effector assembly 301 for holding and/or operating a tool 314 removably attached to the flange 312 by way of an end-effector mount 313. The base 308 may include an actuator to adjust the height of the robotic arm 310. The base may further include a set of wheels 317 to maneuver the base 308, which may be fixed into position using a braking mechanism such as a hydraulic brake. The manipulator arm 310 includes various joints and links to manipulate the tool 314 in various degrees of freedom. If a mechanical digitizer 318 or optical tracking system 306 is not present, the tool 314 may be fitted with a probe tip to collect points on the recovery markers (100, 110) directly. The joints are illustratively prismatic, revolute, or a combination thereof.

The computing system 304 generally includes a planning computer 314; a device computer 316; a tracking computer 336 if a tracking system 306 is present; and peripheral devices. The planning computer 314, device computer 316, and tracking computer 336, may be separate entities, single units, or combinations thereof depending on the surgical system. The peripheral devices allow a user to interface with the surgical system components and may include: one or more user-interfaces, such as a display or monitor 318; and user-input mechanisms, such as a keyboard 320, mouse 322, pendent 324, joystick 326, foot pedal 328, or the monitor 318 in some inventive embodiments have touchscreen capabilities.

The planning computer 314 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. The data generated from the planning computer 314 may be transferred to the device computer 316 and/or tracking computer 336 through a wired or wirelessly connection in the operating room (OR); or transferred via a non-transient data storage medium (e.g., a compact disc (CD), a portable universal serial bus (USB) drive) if the planning computer 314 is located outside the OR.

The device computer 316 in some inventive embodiments is housed in the moveable base 208 and contains hardware, software, data and utilities that are preferably dedicated to the operation of the surgical device 302. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, and utilizing position and orientation (POSE) data from the tracking system 306.

The optional tracking system 306 of the surgical system 300 includes two or more optical receivers 330 to detect the position of fiducial markers (e.g., retroreflective spheres, active light emitting diodes (LEDs)) uniquely arranged on rigid bodies. The fiducial markers arranged on a rigid body are collectively referred to as a fiducial marker array 332, where each fiducial marker array 332 has a unique arrangement of fiducial markers, or a unique transmitting wavelength/frequency if the markers are active LEDs. An example of an optical tracking system is described in U.S. Pat. No. 6,061,644. The tracking system 306 may be built into a surgical light, located on a boom, a stand 342, or built into the walls or ceilings of the OR. The tracking system computer 336 may include tracking hardware, software, data and utilities to determine the POSE of objects (e.g., bones B, surgical device 304) in a local or global coordinate frame. The POSE of the objects is collectively referred to herein as POSE data, where this POSE data may be communicated to the device computer 316 through a wired or wireless connection. Alternatively, the device computer 316 may determine the POSE data using the position of the fiducial markers detected from the optical receivers 330 directly.

The POSE data is determined using the position data detected from the optical receivers 330 and operations/processes such as image processing, image filtering, triangulation algorithms, geometric relationship processing, registration algorithms, calibration algorithms, and coordinate transformation processing. For example, the POSE of a digitizer probe 338 with an attached probe fiducial marker array 332b may be calibrated such that the probe tip is continuously known as described in U.S. Pat. No. 7,043,961. The POSE of the tool tip or tool axis of the tool 114 may be known with respect to a device fiducial marker array 332a using a calibration method as described in U.S. Provisional Patent Application No. 62/128,857. The device fiducial marker 332a is depicted on the manipulator arm 310 but may also be positioned on the base 308 or the end-effector assembly 301. Registration algorithms may be executed to determine the POSE and coordinate transforms between a bone B, a fiducial marker array 332c or 332d, and a surgical plan, using the registration methods described in U.S. Pat. No. 6,033,415, and 8,287,522.

Upon assembly of the device tracking array 332a to the surgical robot 302 prior to surgery, the POSE's of the coordinate systems, 332a and the end effector tool 314, are fixed relative to each other and stored in memory to accurately track the end effector tool 314 during the surgery (see for example U.S. Patent Publication 20140039517 A1) relative to the bone anatomy (e.g., bones B). The POSE data may be used by the computing system 304 during the procedure to update the bone and surgical plan coordinate transforms so the surgical robot 302 can accurately execute the surgical plan in the event any bone motion occurs. However, if there is unintentional movement between the fiducial marker arrays (332c, 332d) and the bone B after initially registering the bone B, then the bone needs to be re-registered to re-establish the coordinate systems between the fiducial marker arrays (332c, 332d) and the bone B. It should be appreciated that in certain embodiments, other tracking systems may be incorporated with the surgical system 300 such as an electromagnetic field tracking system or a 6-DOF mechanical tracking system. An example of a 6-DOF mechanical tracking system is described in U.S. Pat. No. 6,322,567. In a particular inventive embodiment, the surgical system 300 does not include a tracking system 306, but instead employs a bone fixation and monitoring system that fixes the bone directly to the surgical robot 302 in the robotic coordinate frame and monitors bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method for re-registration between a robotic coordinate system and an image data set, said method comprising:
   providing an image data set that has been registered within a robotic coordinate system based upon an initial bone position with the robotic coordinate system;
   providing a first recovery marker and a second recovery marker installed in the bone, said second recovery marker having an elongated groove that facilitates a collection of a series of points along the groove;
   sliding a distal end of a digitizer in the elongated groove to collect a series of points, the digitizer selected from the group consisting of: a mechanical digitizing arm, a robotic arm, and a tracked probe;
   locating a point and a line fixed relative to the initial bone position wherein the point is located by contacting the distal end against a point on the first recovery marker and the line is defined using the series of points collected in the groove;
   relocating the point and at least a portion of the line after bone motion may have occurred to calculate a locational change of the point and the line; and
   re-registering the image data set within the robotic coordinate system based on the locational change.

2. The method of claim 1, wherein at least one of the first or second recovery markers is implanted after the image data set has been created.

3. The method of claim 1, wherein at least one of the first or second recovery markers is attached intraoperatively to the bone.

4. A system for performing the registration recovery method of claim 1 comprising:
   the first recovery marker configured to be installed in the bone at a first position;
   the second recovery marker configured to be installed in the bone at a second position, wherein the second recovery marker comprises the elongated groove for sliding a distal end of a tracked probe therein to facilitate a collection of a series of points; and
   wherein the tracked probe is tracked by a tracking system for collecting the point on the first recovery marker and the series of points in the elongated groove on the second recovery marker.

5. The system of claim 4 further comprising:
   a fiducial marker array configured to be fixed to the bone;

a bone pin; and a pin clamp simultaneously engaging said second recovery marker and said bone pin in a fixed relative orientation when said second recovery marker and said bone pin are configured to be attached to the bone wherein said fiducial marker array extends from said pin clamp.

6. The system of claim 5 wherein said fiducial marker array extends from said pin clamp via an array clamp.

7. The system of claim 6 wherein said array clamp is adjustable as to orientation.

8. The system of claim 4 further comprising a computer for calculating the re-registration of the bone.

9. A system for performing the registration recovery method of claim 1 comprising:

the first recovery marker configured to be installed in the bone at a first position;

the second recovery marker configured to be installed in the bone at a second position, wherein the groove second recovery marker comprises the elongated groove; and a robotic system positioned adjacent to the bone having at least one of the robotic arm and the mechanical digitizer arm wherein the robotic arm or digitizer arm are used to collect a point on the first recovery marker and the series of points in the elongated groove on the second recovery marker.

10. The system of claims 9 wherein the robotic system comprises robotic arm and the mechanical digitizer arm wherein the mechanical digitizer arm is used to collect the on the first recovery marker and the series of points on the second recovery marker.

11. The system of claims 9 wherein the bone is fixed relative to a robotic coordinate frame of the robotic system.

12. The system of claim 9 further comprising a computer to calculate the re-registration of the bone.

13. The method of claim 1 wherein the image data set comprises at least one of an image of the bone or a model of the bone.

* * * * *